United States Patent
Johnson et al.

(12) 
(10) Patent No.: US 10,738,986 B1
(45) Date of Patent: Aug. 11, 2020

(54) LIGHTING DEVICE THAT INTERFACES WITH A COMMUNICATION DEVICE

(71) Applicant: Pyllr, LLC, Dallas, TX (US)

(72) Inventors: Darian Bradwick Johnson, Dallas, TX (US); Philip G. Burger, Dallas, TX (US)

(73) Assignee: Pyllr, LLC, Dallas, TX (US)

( * ) Notice: Subject to any disclaimer, the term of this patent is extended or adjusted under 35 U.S.C. 154(b) by 0 days.

(21) Appl. No.: 16/265,378

(22) Filed: Feb. 1, 2019

(51) Int. Cl.
| | |
|---|---|
| *F21V 23/04* | (2006.01) |
| *F21S 6/00* | (2006.01) |
| *F21S 10/04* | (2006.01) |
| *A61L 9/03* | (2006.01) |
| *F21S 9/02* | (2006.01) |
| *H05B 47/19* | (2020.01) |
| *H05B 47/105* | (2020.01) |
| *F21Y 115/10* | (2016.01) |
| *F21Y 113/13* | (2016.01) |
| *H05B 45/20* | (2020.01) |

(52) U.S. Cl.
CPC ............ *F21V 23/0442* (2013.01); *A61L 9/03* (2013.01); *F21S 6/001* (2013.01); *F21S 9/02* (2013.01); *F21S 10/04* (2013.01); *F21V 23/045* (2013.01); *F21V 23/0485* (2013.01); *F21V 23/0492* (2013.01); *H05B 47/105* (2020.01); *H05B 47/19* (2020.01); *A61L 2209/12* (2013.01); *F21Y 2113/13* (2016.08); *F21Y 2115/10* (2016.08); *H05B 45/20* (2020.01)

(58) Field of Classification Search
CPC .......... F21S 10/04; F21S 10/043; F21S 6/001; F21S 9/02; F21V 23/0485; F21V 23/045; F21V 23/0492; F21V 23/0442; H05B 37/0272; H05B 37/0227; H05B 47/105; A61L 2209/111; A61L 2209/12; A61L 9/03

See application file for complete search history.

(56) References Cited

U.S. PATENT DOCUMENTS

| | | | | |
|---|---|---|---|---|
| 7,997,772 | B2 * | 8/2011 | Avtzon | H05B 45/20 362/392 |
| 8,210,708 | B2 * | 7/2012 | Hau | H02J 50/10 362/183 |
| 9,585,980 | B1 * | 3/2017 | Li | F21S 6/001 |
| 2005/0169812 | A1 * | 8/2005 | Helf | A01M 1/04 422/123 |
| 2005/0285538 | A1 * | 12/2005 | Jaworski | A61L 9/037 315/76 |

(Continued)

OTHER PUBLICATIONS

Caseta by Lutron Smart Home App, Website, screenshot captured on Mar. 25, 2019, pp. 1-2, Luton Electronics Co., Inc., https://www.casetawireless.com/smart-living.

(Continued)

*Primary Examiner* — Erin Kryukova
(74) *Attorney, Agent, or Firm* — Hitchcock Evert LLP (57) ABSTRACT

This invention relates to a lighting device that interfaces with an external communication device. The lighting device assembly comprises a plurality of lighting devices that may contain light sources and control and network modules, which allow for manual and remote operation of the lighting device assembly by a communicatively coupled network. The lighting devices do not contain a flame and are designed to be safer than candles.

19 Claims, 7 Drawing Sheets

(56) References Cited

U.S. PATENT DOCUMENTS

| | | | |
|---|---|---|---|
| 2008/0038156 A1* | 2/2008 | Jaramillo | A01M 1/2072 422/124 |
| 2008/0117633 A1* | 5/2008 | Li | F21S 6/001 362/253 |
| 2008/0130266 A1* | 6/2008 | DeWitt | A61L 9/03 362/96 |
| 2013/0329406 A1* | 12/2013 | Lederer | F21S 6/001 362/183 |
| 2014/0286024 A1* | 9/2014 | Li | F21S 10/04 362/392 |
| 2017/0067608 A1* | 3/2017 | Patton | F21S 10/046 |
| 2018/0066840 A1* | 3/2018 | Bianchini | F23D 3/02 |
| 2019/0128490 A1* | 5/2019 | Boucher | F21S 6/001 |
| 2020/0067331 A1* | 2/2020 | McMurry | H02J 7/0045 |

OTHER PUBLICATIONS

12ct Lumabase Amber Battery Operated LED Votive Candles, Website, screenshot captured on Mar. 25, 2019, pp. 1-4, Target Brands, Inc., https://www.target.com/p/12ct-lumabase-amber-battery-operated-led-votive-candles/-/A-50790797.

Dual Pack E26, Website, screenshot captured on Mar. 25, 2019, pp. 1-7, Signify Holding d/b/a Philips Lighting, https://www2.meethue.com/en-us/p/hue-white-doublepack-e26/046677530372.

Wemo Smart Light Switch, Website, screenshot captured on Mar. 25, 2019, pp. 1-6, Belkin International, Inc., https://www.belkin.com/us/p/P-F7C030/.

\* cited by examiner

LIGHTING DEVICE THAT INTERFACES WITH A COMMUNICATION DEVICE

FIELD OF THE DISCLOSURE

The invention relates generally to the field of lighting devices.

BACKGROUND

Open-flame candles cause fires and property damage because they can easily be knocked over, and a draft of air can push a flammable material into the flame.

Existing flameless candles do not resemble candles. Nor do they emit a pleasant scent like a candle. Electric wax warmers also pose fire hazards, and oftentimes, they do not melt the wax quickly.

SUMMARY

The present disclosure teaches a lighting device that is flameless and is designed to resemble a flickering candle. In some embodiments, the lighting device assembly has a plurality of light devices that are operably connected to a base. The lighting device may be designed from a translucent material, may be powered by an internal or external power source, and may have an embedded retainer and light source. The lighting device assembly may include a heat source that heats and melts a scented material. Several features of the lighting device assembly, such as the translucent material, embedded retainer and heating of scented material, are designed to give the lighting devices certain qualities of candles.

The lighting device assembly incorporates buttons, sensors and modules for controlling operations of the lighting devices in some embodiments. For example, motion sensors, temperature sensors, power sensors, and optical sensors may facilitate safety, operation management, and power management features by allowing a control module to limit operation of the lighting device assembly. The lighting device may additionally incorporate a network module to allow the lighting device to interface with an external communication device that is communicatively coupled to a network.

Additional aspects, advantages and features are included in the following description of examples. The description should be taken in conjunction with the accompanying figures, wherein like numerals are used to describe the same feature throughout the figures.

A BRIEF DESCRIPTION OF THE DRAWINGS

Embodiments will now be described, by way of example only, with references to the accompanying drawings in which.

DETAILED DESCRIPTION

While this invention may be embodied in many different forms, there will herein be described in detail preferred embodiments of the invention with the understanding that the present disclosure exemplifies the principles of the invention and is not intended to limit the broad aspects of the invention to the embodiments illustrated. It will be understood that the invention may be embodied in other specific forms without departing from the spirit or central characteristics thereof. Therefore, the present embodiments should be considered in all respects as illustrative and not restrictive, and the invention is not to be limited to the details given herein.

Figure 1:
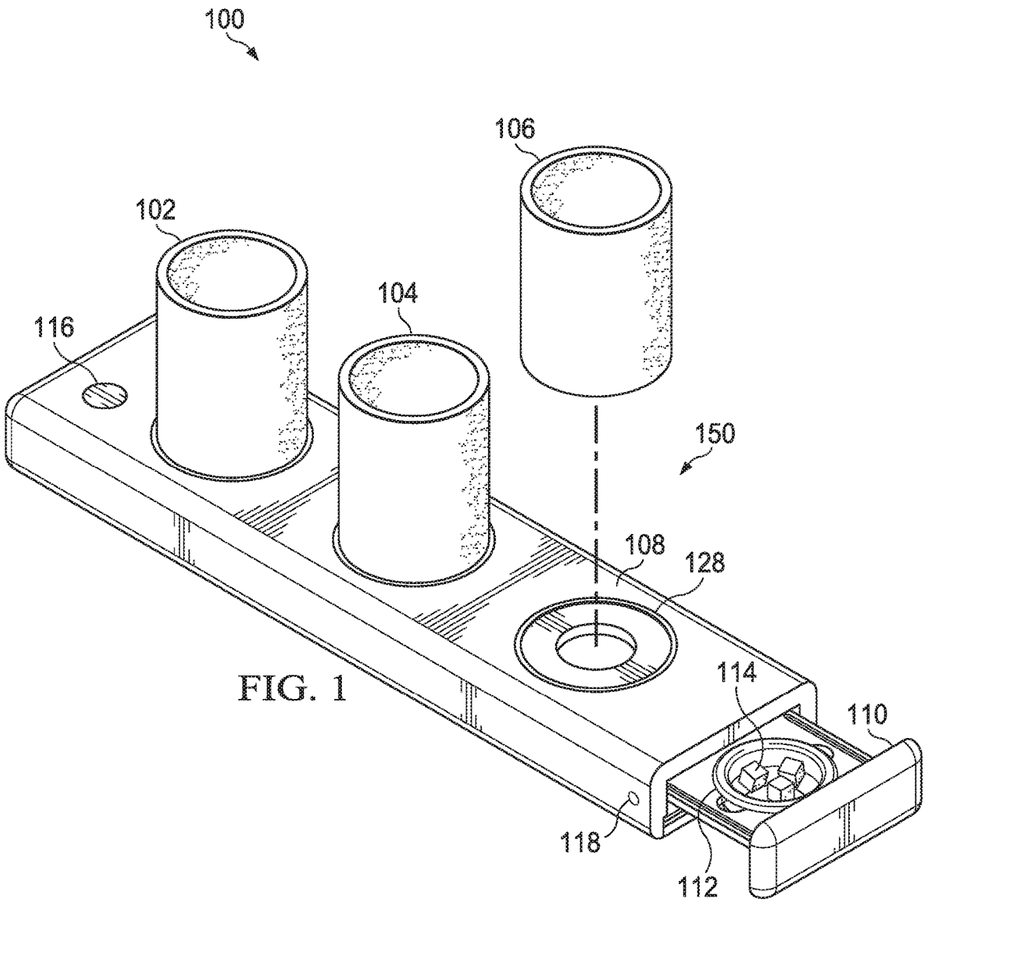
FIG. 1 is a perspective view of an embodiment of a lighting device assembly.

FIG. 1 illustrates a lighting device assembly 100 having a plurality of lighting devices 102, 104 and 106. The number of lighting devices may vary. For example, lighting device assembly 100 may have one or more lighting devices 102, 104 and 106.

Lighting devices 102, 104 and 106 may be designed from any single or combination of translucent or semi-translucent materials, such as wax, plastic, silicone, acrylic and glass, that allow(s) light to be diffused across the surfaces of lighting devices 102, 104 and 106. In some embodiments, the material may comprise a single wax or a mixture of waxes, including but not limited to, paraffin, microcrystalline, petrolatum, beeswax, palm, and vegetable wax. For example, lighting devices 102, 104 and 106 may comprise a mixture of approximately 90-95% of Parafflex® wax and 5-10% of microcrystalline wax.

Lighting devices 102, 104 and 106 may have a single color or multiple colors. In some instances, a user may possess a plurality of lighting devices having various colors for interchangeability. For example, a user may replace white lighting devices 102, 104 and 106 with red lighting devices 102, 104 and 106 during the holiday season.

Lighting devices 102, 104 and 106 are operably connected to a base 150. In this embodiment, lighting devices 102, 104 and 106 are configured to be removable from base 150. Lighting devices 102, 104 and 106 may be operably connected to base 150 by friction, adhesion, magnetism, hook and loop tape, straps, snaps, locks, threads, and other connections. The type of removable connection may vary.

Lighting devices 102, 104 and 106 may be operable when connected to base 150 and when removed from base 150. Lighting devices 102, 104 and 106 may be operably connected to base 150 by a physical connection, such as a wired connection. In some embodiments, lighting devices 102, 104 and 106 may also include an internal power source (such as lighting device 200 shown in FIG. 5). A user may remove a single lighting device 106 that includes an internal power source from base 150. Upon removal from base 150, lighting device 106 will switch to a wireless mode, in which lighting device 106 will communicatively couple to lighting device assembly 100 by a wireless connection while lighting devices 102 and 104 will communicatively couple to lighting device assembly 100 by a physical connection.

In some embodiments, lighting devices 102, 104 and 106 are operably connected to base 150 by a permanent or semi-permanent connection, such as a bolt, screw, pin, and other connections. The connection may be threaded, welded, wired, or another type of connection. Again, the type of permanent or semi-permanent connection may vary.

The base 150 further comprises a sliding member 110. Sliding member 110 contains a vessel 112 that comprises a heat-resistant and non-porous material, such as ceramic, glass and aluminum. In some embodiments, vessel 112 is not flammable and does not leak or crack during operation of lighting device assembly 100.

Vessel 112 contains a scented material 114 that may be a solid at room temperature. The scented material 114 may be comprised of a single or a mixture of waxes, such as paraffin, microcrystalline, petrolatum, beeswax, palm, and vegetable wax. The scented material 114 may have a melting point between 120 and 180 degrees Fahrenheit. For example, scented material 114 may melt at approximately 130 degrees Fahrenheit. When heated, scented material 114 melts and emits a scent. In some embodiments, the scented material 114 comprises a biodegradable and renewable resource, such as soy wax. Scented material 114 is shown as being a cubical shape, but may be any other shape, such as spherical, rounded, cylindrical, and the like. For example, scented material 114 may be in the shape of a pellet.

Base 150 may connect to an external power source (not shown), such as a wall socket. In addition, base 150 may connect to an external communication device by a cable, such as USB, USB-C, mini-USB, micro-USB, and the like. In other embodiments, base 150 or lighting devices 102, 104 and 106 may be powered by an internal power source, such as a battery. The battery may be recharged by connecting to a wall socket, a wireless charger, or any other type of charger.

Lighting device assembly 100 also has a button 116 on a top section 108 of base 150. Button 116 may control a single operation or various operations of lighting device assembly 100, such as turning lighting device assembly 100 on and off, changing the colors of lighting devices 102, 104 and 106, and activating a heat source to melt scented material 114. Button 116 may also be configured to allow a user to change the color, brightness and pattern of indicator 118. Although this example shows a single button, other examples may have a plurality of buttons for controlling various operations of lighting device assembly 100, such as dimming a light source or changing the color of indicator 118 from red to yellow. In other embodiments, base 150 may have one or more buttons 116 on a back part, front part, or side part of top section 108 or bottom section 134 (shown in FIG. 2).

Figure 2:
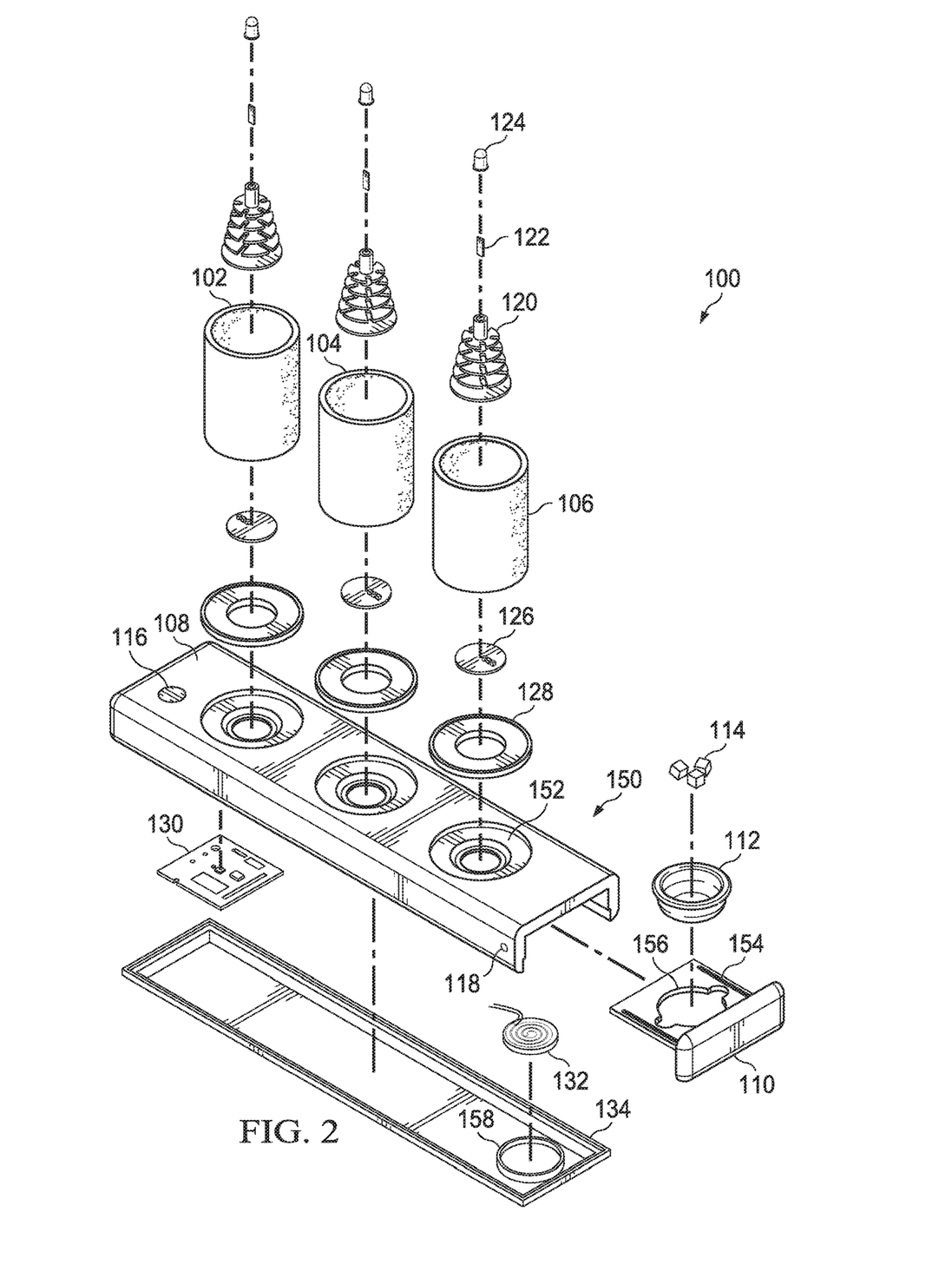
FIG. 2 is an exploded view of the embodiment of the lighting device assembly.
Figure 3:
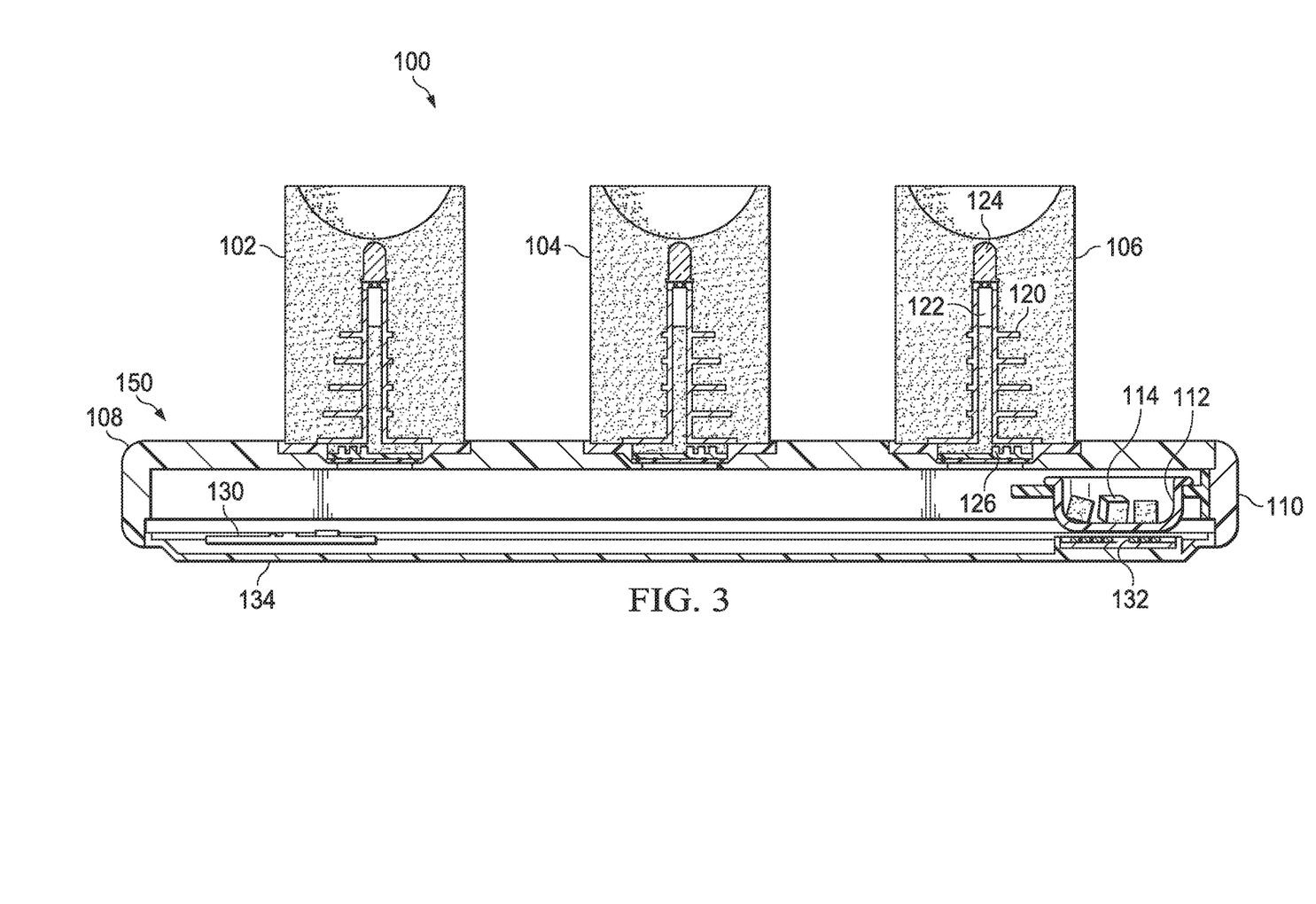
FIG. 3 is a cross-section view of the embodiment of the lighting device assembly.

FIGS. 2 and 3 show an exploded view and a cross-section view of lighting device assembly 100. Lighting device 106 comprises a retainer 120 and an electrical circuit 122 that is connected to a light source 124. Light source 124 may emit a single color or multiple colors. Light source 124 may include a single light emitting diode or a plurality of light emitting diodes (such as an RGB light emitting diode, a NeoPixel® light emitting diode, a DotStar™ light emitting diode, etc.), an incandescent bulb, a fluorescent bulb or other luminous component.

In this embodiment, base 150 comprises a top section 108 and a bottom section 134. Lighting device 106 operably connects to the top section 108 by a supportive covering 128. In some embodiments, supportive covering 128 has an aesthetic or supportive function. Supportive covering 128 is shown as being a circular shape, but may be any other shape, such as elliptical, polygonal, and the like. Supportive covering 128 may provide additional support for lighting devices 102, 104 and 106. In other embodiments, lighting device 106 may connect directly to the top section 108 without supportive covering 128.

FIG. 2 also shows a supportive base element 152 that operably connects to supportive covering 128. Supportive base element 152 is recessed and is shown as being a circular shape, but may be any other shape, such as elliptical, polygonal, and the like. The recession of supportive base element 152 may provide additional stability to lighting devices 102, 104 and 106. Other embodiments of lighting device assembly 100 may have a supportive base element 152 that forms a continuous or semi-continuous plane with top section 108.

Top section 108 or bottom section 134 may further comprise horizontal or vertical intermediary sections to partition or conceal circuit board 130, heat source 132 and heat ring 158.

Top section 108 and bottom section 134 may be operably connected by friction, adhesion, magnetism, hook and loop tape, straps, snaps, locks, threads, and other connections. The type of connection may vary. In some embodiments, top section 108 and bottom section 134 are operably connected by a permanent or semi-permanent connection, such as a bolt, screw, pin, and other connections. The connection may be threaded, welded, wired, or another type of connection. Again, the type of permanent or semi-permanent connection may vary.

FIG. 2 also illustrates the heating of scented material 114 in vessel 112 by heat source 132. FIG. 2 depicts a vessel opening 156 for holding vessel 112 in place, but other embodiments may not contain vessel opening 156. In some embodiments, vessel 112 may be operably connected to heat source 132 without an intervening structure or space between vessel 112 and heat source 132.

Heat source 132 may comprise a heating pad, heating mat, heating element, and any other component that is capable of emitting sufficient heat to melt scented material 114. For example, heat source 132 may comprise a coil or strip designed to emit heat between 120 and 180 degrees Fahrenheit, such as between approximately 130 and 140 degrees Fahrenheit. During operation of heat source 132, a user places scented material 114 in vessel 112 and closes sliding member 110, which connects to the inside surfaces of the front part and back part of top section 108 by groove 154. In some embodiments, sliding member 110 may connect to the top section 108 and bottom section 134 by another connection, such as friction, adhesion, magnetism, hook and loop tape, straps, snaps, locks, threads, and other connections. In other embodiments, sliding member 110 may partially slide into top section 108, or sliding member 110 may not slide into top section 108 at all. For example, vessel 112 may be held in place by a stationary member that is accessible from a top part of section 108. As another example, sliding member 110 may be connected to or form a part of top section 108 or bottom section 134.

Heat source 132 may connect to heat ring 158 by friction, adhesion, magnetism, hook and loop tape, straps, snaps, locks, threads, and other connections. In some embodiments, heat ring 158 provides support for and holds heat source 132 in place. Other embodiments may not include heat ring 158, allowing heat source 132 to connect directly to bottom section 134. Heat source 132 may be activated manually by button 116 or remotely via an external communication device.

The size and shape of heat source 132 may also vary. Heat source 132 is shown as being a circular shape, but may be any other shape, such as elliptical, polygonal and the like. In addition, heat source 132 may extend further along base 150. For example, heat source 132 may extend toward circuit board 130, underneath lighting devices 102, 104 and 106.

Lighting device assembly 100 also comprises a plurality of circuit boards for controlling various operations of lighting device assembly 100, such as activating and deactivating light source 124 and heat source 132 and customizing the color, brightness and pattern of indicator 118. FIG. 2 includes a circuit board 126 in lighting device 106 and a circuit board 130 in base 150. In other embodiments, lighting device assembly 100 may have a single circuit board or a plurality of circuit boards mounted in base 150 and lighting devices 102, 104 and 106.

In this embodiment, lighting devices 102, 104 and 106 each include a circuit board for controlling the operation of each lighting device 102, 104 106. But only the circuit board 126 in lighting device 106 will be discussed herein because the circuit boards in lighting devices 102 and 104 may be configured in a similar manner.

Circuit board 130 includes a microcontroller and a control module that controls features of lighting device assembly 100, such as light source 124, heat source 132, indicator 118, etc. For example, a user may activate button 116 to turn on lighting device 106. Once the button 116 is activated, data is sent to the control module, which transmits data to and illuminates the light source 124. In some embodiments, activating button 116 will turn on lighting devices 102, 104 and 106 of lighting device assembly 100. As another example, button 116 may be activated to turn on heat source 132. The control module may turn on heat source 132 based on an input to button 116.

A user may also activate button 116 to communicatively couple to a wireless network. When the lighting device has coupled to a wireless network, indicator 118 may illuminate to tell a user that lighting device assembly 100 is communicatively coupled with a network or with an external communication device.

This embodiment also includes a circuit board 126 that includes a network module for allowing lighting device 106 to communicatively couple to a wireless network and permitting a user to control the operation of lighting device assembly 100 via the wireless network. The wireless network may be cellular (e.g., 2G, 3G, 4G, 5G, long-term evolution, etc.), Bluetooth®, ZigBee®, Wi-Fi, and other networks.

For example, a user may verbally instruct an external communication device to illuminate lighting device 106. Upon receiving the audio input, the external communication device may process the audio data and transmit data to the network module in circuit board 126, which turns on light source 124. In some embodiments, the external communication device may determine instructions based on a comparison of the received audio input with data stored in a database on a server.

A user may also verbally instruct an external communication device to illuminate lighting device assembly 100. Upon receiving the audio input, the external communication device may process the audio data and transmit data to the network modules in each circuit board of lighting devices 102, 104 and 106, which turns on a light source in each lighting device. In some embodiments, the network modules in lighting devices 102, 104 and 106 exchange data with each other to facilitate operation of lighting device assembly 100. Similarly, a user may control a plurality of lighting device assemblies 100 via a single user interface, such as an external communication device. One skilled in the art will recognize that a variety of operations may be implemented across networked lighting devices 102, 104 and 106 and lighting device assemblies 100.

In some embodiments, lighting device assembly 100 includes a tilt sensor and a control module. The tilt sensor may facilitate safety features by allowing the control module to limit operation of the lighting device assembly 100 based on a detected tilt of base 150. During operation, the tilt sensor determines whether the base 150 has tilted. For example, the tilt sensor may be configured to allow some minimal tilt, such as the movement that may occur when a user moves lighting device assembly 100 to a different place in a room.

If the tilt exceeds a threshold amount based on the expected tilt of base 150, the control module may determine that base 150 has tilted to such a degree that vessel 112 may become dislodged and terminate one or more features (e.g., heat source 132, light source 124, indicator 118, etc.) to decrease the risk of fire and damage to lighting device assembly 100 and property near lighting device assembly 100. The tilt sensor may continuously detect tilt, and the control module may resume operation of one or more features associated with the user's prior setting selection when the tilt detected by the tilt sensor indicates that the tilt sensor is approximately parallel to the bottom section 134 or a bottom of base 150.

As another example, lighting device assembly 100 may comprise a control module and a detachment sensor, such as a magnetic field sensor, an electric conduction sensor, or any other sensor that is capable of detecting a sufficient detachment of lighting devices 102, 104 and 106 from base 150. The detachment sensor may facilitate power management features by allowing the control module to limit operation of the lighting device assembly 100 based on a detachment of lighting devices 102, 104 and 106 from base 150. In this embodiment, the detachment sensor detects when lighting device 106 has been detached from supportive covering 128. For example, if lighting device 106 is detached from supportive covering 128, then the control module may terminate one or more features (e.g., heat source 132, light source 124, indicator 118, etc.) to conserve power or efficiently utilize a power source. In some embodiments, if lighting device 106 is detached from supportive covering 128, then the lighting device 106 may switch to a wireless mode and utilize power from an internal power source, such as a battery.

In other embodiments, lighting device assembly 100 includes an accelerometer and a control module. The accelerometer may facilitate safety features by allowing the control module to limit operation of the lighting device assembly 100 based on a detected change in acceleration of base 150 relative to freefall. During operation, the accelerometer determines whether the acceleration of lighting device 106 or base 150 has increased. For example, if the acceleration exceeds a threshold amount based on the expected acceleration of base 150, then the control module may determine that base 150 has accelerated to such a degree that vessel 112 may become dislodged and terminate one or more features (e.g., heat source 132, light source 124, indicator 118, etc.) to decrease the risk of fire and damage to lighting device assembly 100 and property near lighting device assembly 100. By way of example, the acceleration of base 150 may increase if lighting device assembly 100 falls from a table, shelf, or other surface.

In some embodiments, lighting device assembly 100 further comprises a network module. The tilt sensor, detachment sensor and accelerometer may be communicatively coupled to the network module and the control module by a wireless network. For example, when the control module terminates one or more features of lighting device assembly 100, the control module may transmit data to the network module, which exchanges data with an external communication device to tell a user via a user interface of the external communication device that base 150 moved and that operation of lighting device assembly 100 was terminated. In some embodiments, the tilt sensor, detachment sensor and accelerometer are communicatively coupled to the control module by a wired connection, such as a wire, cable, etc. One skilled in the art will recognize that other movement detectors may be used with or instead of the tilt sensor, motion sensor and accelerometer to facilitate safety features based on the movement of lighting device assembly 100.

FIG. 2 also comprises an indicator 118 as a visual output to indicate a status of lighting device assembly 100. Indicator 118 may comprise a light source, such as a single light emitting diode, a plurality of light emitting diodes, an incandescent bulb, a fluorescent bulb or other luminous component. After receiving data from circuit board 126 and/or 130, indicator 118 may emit a constant light or an intermittent pattern of light, such as dimming, blinking, and flickering. Indicator 118 may show a user whether vessel 112 is warm. Indicator 118 may also show whether lighting device assembly 100 is communicatively coupled to a wireless network or an external communication device. In some embodiments, lighting device assembly 100 comprises a plurality of indicators 118, each of which may receive data from circuit board 126 and/or 130 and to emit a single color or multiple colors. In this example, indicator 118 is placed on a front part of top section 108, but indicator 118 may also be placed on a back part, top part, or side part of top section 108 or bottom section 134. In some embodiments, other outputs may be used with or instead of the visual output, such as audible outputs, mechanical outputs and other outputs.

In other embodiments, lighting device assembly 100 includes a temperature sensor in or near heat source 132 and a control module on circuit board 130. The temperature sensor may facilitate safety features by allowing the control module to control operation of the lighting device assembly 100 based on the temperature of heat source 132. The temperature sensor may be connected to heat source 132, or it may be located near vessel 112 or sliding member 110.

For example, the temperature sensor may measure the temperature of heat source 132. If the temperature is above a threshold temperature based on the temperature at which the vessel 112 may burn a user (such as a temperature above 120 degrees Fahrenheit), then the control module may transmit data to indicator 118. Upon receiving that data, indicator 118 may illuminate to tell the user that vessel 112 is warm. Alternatively, the control module may determine that vessel 112 is above a threshold temperature that may risk the user's safety (such as a temperature above 220 degrees Fahrenheit), terminate operation of lighting device assembly 100 and provide a warning to the user via indicator 118. In other embodiments, the user may receive a warning via an external communication device.

As another example, the control module may terminate operation of lighting device assembly 100 based on a period of time. For example, the control module may determine that a feature of lighting device assembly 100, such as heat source 132, has been activated for a period of three hours and terminate operation of heat source 132. The period of time may be lower or higher based on the amount of scented material 114 in vessel 112 or based on a user's setting selection. For instance, a user may verbally instruct an external communication device to activate light source 124 for a period of four hours. Upon receiving the audio input, the external communication device processes the audio data and transmits data to a network module on circuit board 126, activating light source 124. When the control module determines that a period of four hours has elapsed, the control module may deactivate light source 124. In some embodiments, the external communication device may determine instructions based on a comparison of the received audio input with data stored in a database on a server.

In other embodiments, the temperature sensor may measure the temperature of lighting device assembly 100 when a user activates button 116 or transmits an input to an external communication device. For example, a user may desire to know information about the temperature of heat source 132, vessel 112 or scented material 114. The user may transmit an input to an external communication device, which exchanges data with lighting device assembly 100 via a wireless network, after which temperature data is transmitted to a user interface of an external communication device. The user interface may transmit a visual or audio output to the user.

Based on the temperature data, a user may desire to modify the temperature of heat source 132. To increase or decrease the temperature, the user may activate button 116 or transmit an input to an external communication device that will exchange data with lighting device assembly 100 over a communicatively coupled network.

In some embodiments, the temperature sensor and control module may measure and determine the temperature of heat source 132 during a series of intervals to conserve power. In other embodiments, the temperature sensor continuously detects the temperature of heat source 132. For example, during operation of lighting device assembly 100, the temperature sensor may detect an increase in the temperature of heat source 132 and transmit that data to the control module, which transmits data to indicator 118 so that indicator 118 will illuminate in a yellow color to tell the user heat source 132 has been activated. As another example, if the temperature sensor detects a spike in temperature, the control module may determine that the amount of scented material 114 in vessel 112 has decreased and transmit that information to the user via indicator 118 or a user interface on an external communication device.

When the temperature sensor determines that heat source 132 is above a threshold temperature that may burn a user, the control module may transmit data to indicator 118 so that indicator 118 will illuminate in a red color or blinking pattern to indicate that vessel 112 is hot and that the user may desire to exercise caution when opening sliding member 110. The color, brightness, and pattern of indicator 118 may vary. In some embodiments, other outputs may be used with or instead of the visual output, such as audible outputs, mechanical outputs and other outputs.

In some embodiments, the temperature sensor is communicatively coupled to the control module by a wire. In other embodiments, the temperature sensor is communicatively coupled to the control module by a wireless network. One skilled in the art will recognize that other temperature detectors may be used with or instead of the temperature sensor to facilitate safety features based on the temperature of lighting device assembly 100.

In some embodiments, the heat emitted from components in the bottom section 134, such as circuit board 130, may heat vessel 112 to a temperature, such as between 70 and 100 degrees Fahrenheit, that softens, but does not melt, scented material 114. For example, the components may emit heat at approximately 80 to 90 degrees Fahrenheit. This pre-heating of scented material 114 decreases the amount of time between a user activating heat source 132 and the scented material 114 melting in vessel 112 and emitting a desired scent. Circuit board 130 may also contain a heat sink for dissipating excess heat emitted from the various components in the bottom section 134. For example, a heat sink associated with circuit board 130 may be designed to dissipate excess heat for the pre-heating of scented material 114. Circuit boards 126 and 130 may further incorporate various transistors, voltage regulators, resistors, capacitors, and the like for efficient operation of lighting device assembly 100.

Other embodiments of lighting device assembly 100 include a level sensor and a control module. The level sensor may facilitate operation management features by allowing the control module to limit operation of the lighting device assembly 100 based on a detected change in the level of scented material 114 in vessel 112. The level sensor may be connected to or located near vessel 112 or sliding member 110. If the level of scented material 114 is below a threshold amount (such as an amount needed for the efficient emission of a scent), then the control module may determine that more scented material 114 should be added to vessel 112 and terminate heat source 132 to efficiently operate lighting device assembly 100.

In some embodiments, the control module may monitor consumption of scented material 114 and transmit data to an external communication device to tell the user that the level of scented material 114 has decreased. The level may be continuously monitored or monitored during a series of intervals to conserve power.

In addition, the control module may track a user's orders of scented material 114. For example, when a user orders an amount of scented material 114 via an external communication device, the external communication device exchanges data with the control module so the control module can track the selected amounts. When the level of scented material 114 is below the threshold amount, the control module may determine an amount that a user may desire to order based on the threshold amount or the amount of the user's previous order. The control module then transmits this data to the external communication device, which may be configured to automatically order the amount of scented material 114 determined by the control module. Alternatively, the external communication device may transmit an output to the user, asking the user if he or she would like to order the amount determined by the control module.

In some embodiments, the level sensor is communicatively coupled to the control module by a wire. In other embodiments, the level sensor is communicatively coupled to the control module by a wireless network. One skilled in the art will recognize that other detectors, such as pressure detectors, may be used with or instead of the level sensor to facilitate operation management features based on the level of scented material 114.

Some embodiments of lighting device assembly 100 may have a single microcontroller and a plurality of modules, such as control modules, network modules, etc., mounted on circuit board 126 or 130 whereas other embodiments may have a plurality of microcontrollers on circuit board 126 or 130. In some embodiments, lighting devices 102, 104 and 106 do not include a circuit board or microcontroller. Rather, base 150 may include a circuit board 130, a plurality of microcontrollers and a plurality of modules for controlling the operation of lighting device assembly 100. The number and placement of microcontrollers in lighting device assembly 100 may vary.

Figure 4:
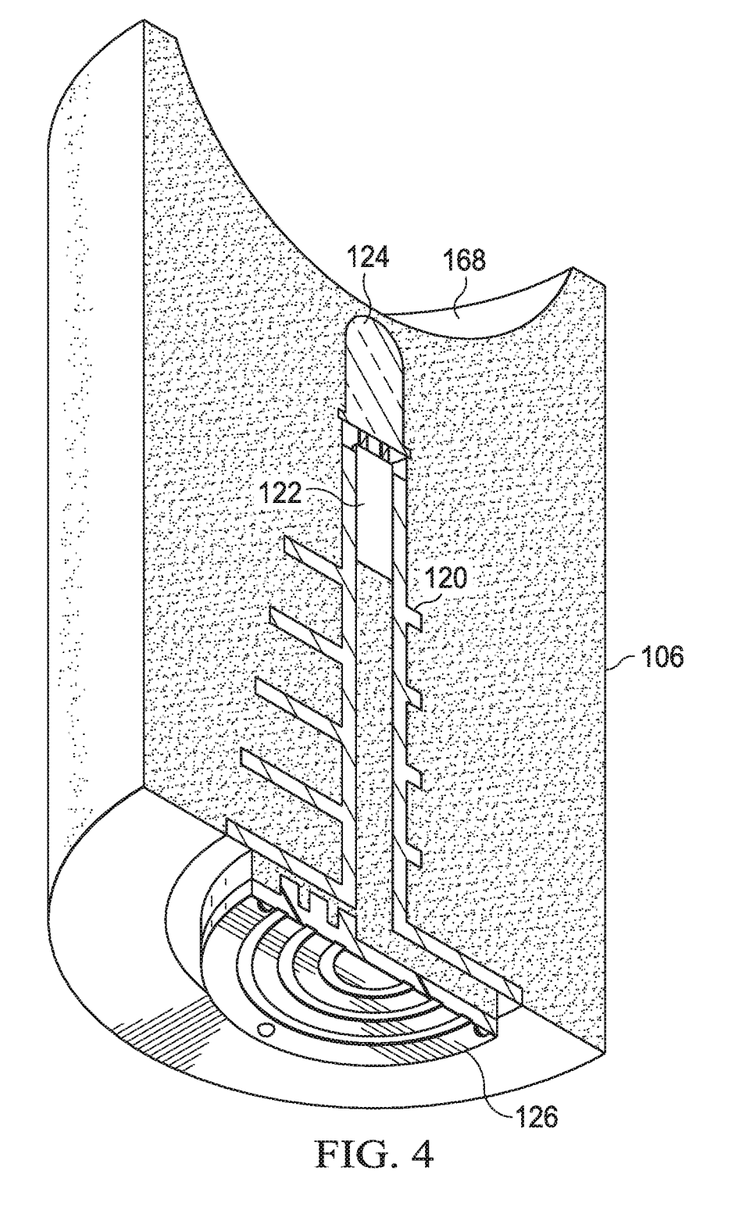
FIG. 4 is a cross-section view of the embodiment of the lighting device.

FIG. 4 illustrates a cross-section view of lighting device 106 removed from base 150. This cross-section view shows a retainer 120 having a plurality of protruding surfaces on a left side and a plurality of indentions on a right side of each concentric ring. The lighting device 106 also has a concave surface 168 that extends to a central area above light source 124. In other embodiments, the space between light source 124 and the concave surface 168 of the central area of lighting device 106 may be larger or smaller depending on the desired appearance. For example, a smaller space may result in a brighter hotspot light whereas a larger space may result in a more diffused light.

This embodiment also depicts light source 124, electrical circuit 122 and retainer 120 as being embedded in lighting device 106. Embedding these components may attribute to the lighting device 106 having an appearance of a flickering candle. A flickering appearance may also be accomplished by mounting a plurality of light sources that illuminate at alternating times and angles. In some embodiments, electrical circuit 122 may control the operation and power of light source 124 to create the flickering appearance. In other embodiments, light source 124 may protrude from the concave surface 168 of lighting device 106.

Electrical circuit 122 is also fully inserted into a light source housing to insulate the electrical components. But other embodiments may allow electrical circuit 122 to be partially exposed.

Figure 5:
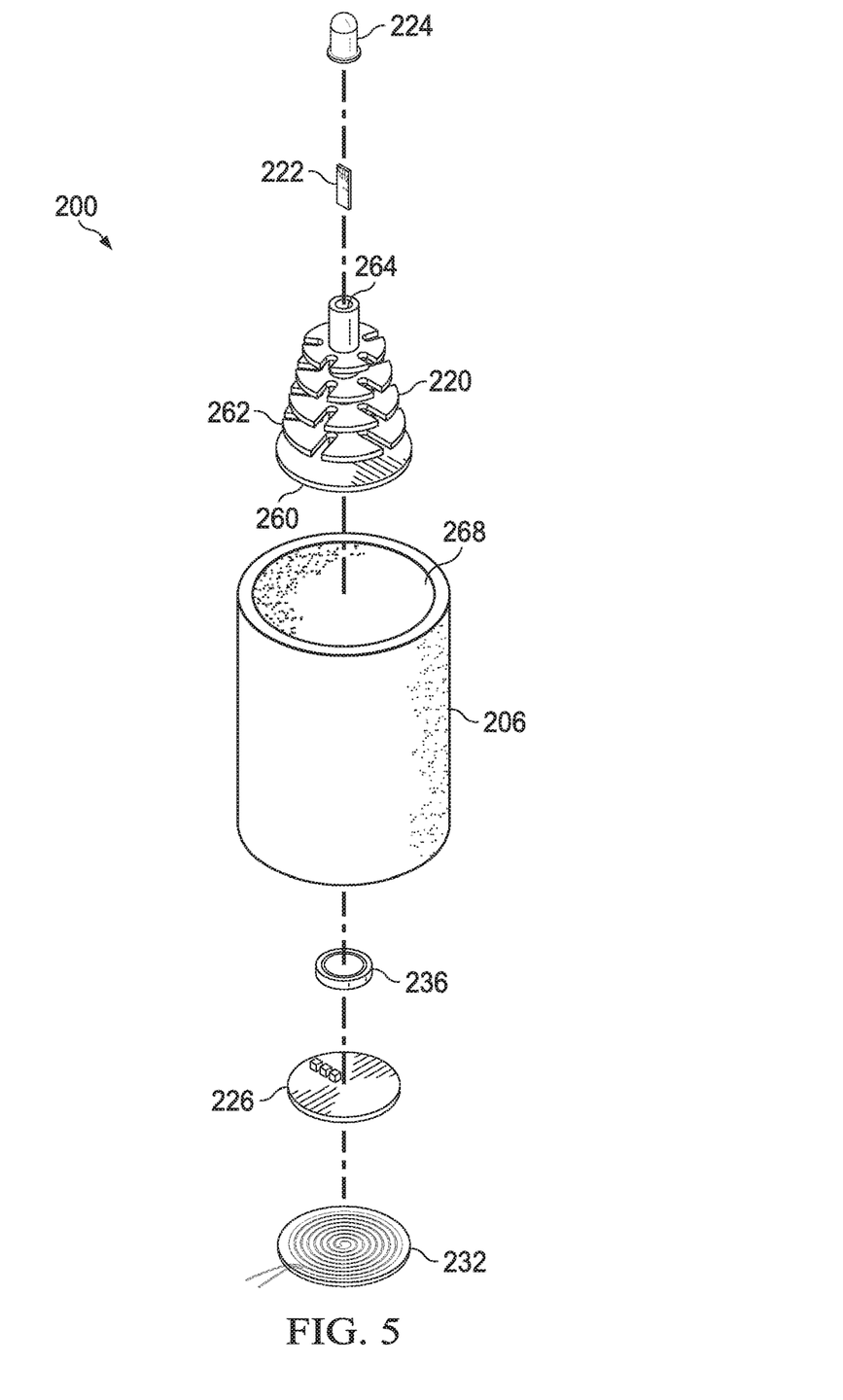
FIG. 5 is an exploded view of another embodiment of a lighting device.

FIG. 5 depicts another embodiment of lighting device 200. Lighting device 200 comprises a light source 224 and an electrical circuit 222 mounted to a light source housing 264 of a retainer 220.

Lighting device 200 may be designed by various techniques, such as 3D printing, injection molding, etc. In some embodiments, retainer 220, light source housing 264, electrical circuit 222 and light source 224 may be inserted into a mold cavity having the same shape and size as lighting device body 206, after which a heated translucent or semi-translucent material, such as wax, plastic, silicone, acrylic and glass, is poured into the mold cavity until the light source 224 and retainer 220 are submerged in the material. After the material cools, the lighting device body 206 is removed from the mold cavity. In some embodiments, a portion of light source 224 or the retainer 220 may remain exposed after the material is poured into the mold cavity.

In some embodiments, retainer 220 may comprise a heat-resistant material, such as plastic, acrylic, ceramic, silicone and glass. Retainer 220 may have a melting point between 210 and 230 degrees Fahrenheit, such as 220 degrees Fahrenheit. But retainer 220 may have a higher or lower melting point depending on the temperature of the translucent or semi-translucent material poured into lighting device 206. Lighting devices 102, 104, 106, 302, 402, 404, and 406 may be designed by the same technique as lighting device 200.

Retainer 220 also comprises a plurality of concentric rings 262 connected to a circular band 260. The number, size and thickness of concentric rings 262 may vary based on the shape and size of lighting device body 206. Each concentric ring 262 further comprises a plurality of indentions along the circumference of concentric rings 262. The indentions in retainer 220 create protruding surfaces to which the translucent or semi-translucent material may adhere, allowing retainer 220 to be held in place throughout operation of lighting device 200.

In other embodiments, retainer 220, light source housing 264, electrical circuit 222 and light source 224 are inserted into a bottom of lighting device body 206. The retainer 220 may be held in place inside lighting device body 206 by a connection, such as friction, adhesion, magnetism, hook and loop tape, straps, snaps, locks, threads, and other connections.

FIG. 5 also illustrates a lighting device 206 that is powered by an internal power source 236, such as a rechargeable battery. Internal power source 236 is operably connected to circuit board 226 and a wireless charging pad 232. To charge internal power source 236, a user may place the wireless charging pad 232 near an external charging station to allow the internal power source 236 to be charged by inductive charging. One having ordinary skill in the art would also appreciate that any of the illustrated lighting devices 102, 104, 106, 302, 402, 404 and 406 may include an internal power source 236 and/or a wireless charging pad 232.

Figure 6:
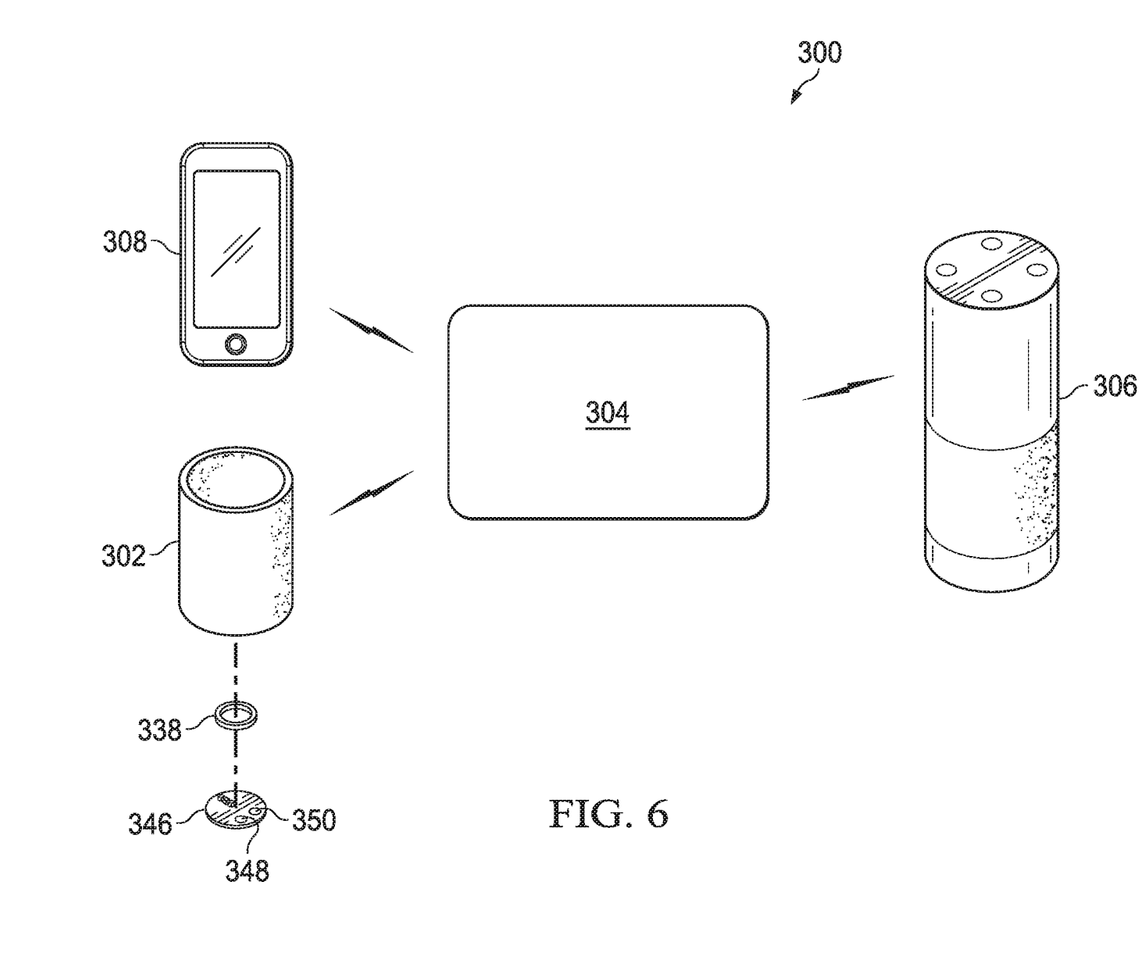
FIG. 6 shows another embodiment of a lighting device assembly interfacing with a plurality of external communication devices.

FIG. 6 depicts a system 300 having lighting devices and external communication devices, including voice-controlled device 306 and phone 308, that are communicatively coupled to a network. Lighting device 302 communicatively couples to external communication devices by a wireless network, such as cellular (e.g., 2G, 3G, 4G, 5G, long-term evolution, etc.), Bluetooth®, ZigBee®, Wi-Fi, and other networks. In other embodiments, lighting device 302 is communicatively coupled to external communication devices by a cable, such as USB, USB-C, mini-USB, micro-USB, and other cables. One skilled in the art will recognize that any means of connecting and coupling components to allow communication signals to be transmitted and received may be implemented.

In the system 300, a circuit board 346 is shown as being communicatively coupled to a server 304 that is also communicatively coupled to a voice-controlled device 306 and a phone 308. The server 304 may be any computing device capable of allowing the lighting device 302 to interface with voice-controlled device 306 and phone 308.

In this embodiment, circuit board 346 includes a network module 348 that allows lighting device 302 to communicatively couple to a wireless network and a control module 350 that allows users to control operations of the lighting device 302 over the wireless network.

The network module 348 allows lighting device 302 to communicatively couple to a wireless network, permitting a user to control operation of lighting device 302 by voice-controlled device 306. For example, a user may speak to voice-controlled device 306 to turn on the light source in lighting device 302. Upon receiving the audio input, the voice-controlled device 306 may process the audio input and transmit data to the network module 348 to allow the microcontroller in circuit board 346 to access the wireless network. In some embodiments, the voice-controlled device 306 may determine instructions based on a comparison of the received audio input with data stored in a database on server 304.

As another example, a user may press a button or touch a screen on phone 308 to activate lighting device 302. Upon receiving the input, the phone 308 may process the input and transmit data to the network module 348 to allow the microcontroller in circuit board 346 to access the wireless network and activate lighting device 302.

It will be understood that lighting device 302 may be controlled by an external communication device regardless of the distance between lighting device 302 and the external communication device. For example, a user may remotely activate via phone 308 a lighting device 302 that is located in a home while the user is miles away at an office.

In some embodiments, lighting device 302 further comprises a power source 338 and a power sensor that facilitates power management features by allowing control module 350 to limit operation of the lighting assembly 100 based on the power level of power source 338. The power sensor may determine the power level of power source 338, and if the power level is below a threshold level, the control module 350 may limit one or more features of lighting device 302. For example, if the power sensor determines the power level is below twenty five percent, the control module may dim the brightness of lighting device body 206 so that it will remain illuminated for a longer period of time. One skilled in the art will recognize that other power detectors may be used with or instead of the power sensor to facilitate power management based on the power level of power source 338.

In some embodiments, the power sensor is operably connected to the control module 350 by a wire or cable. In other embodiments, the power sensor is communicatively coupled to control module 350 by a wireless network.

Figure 7:
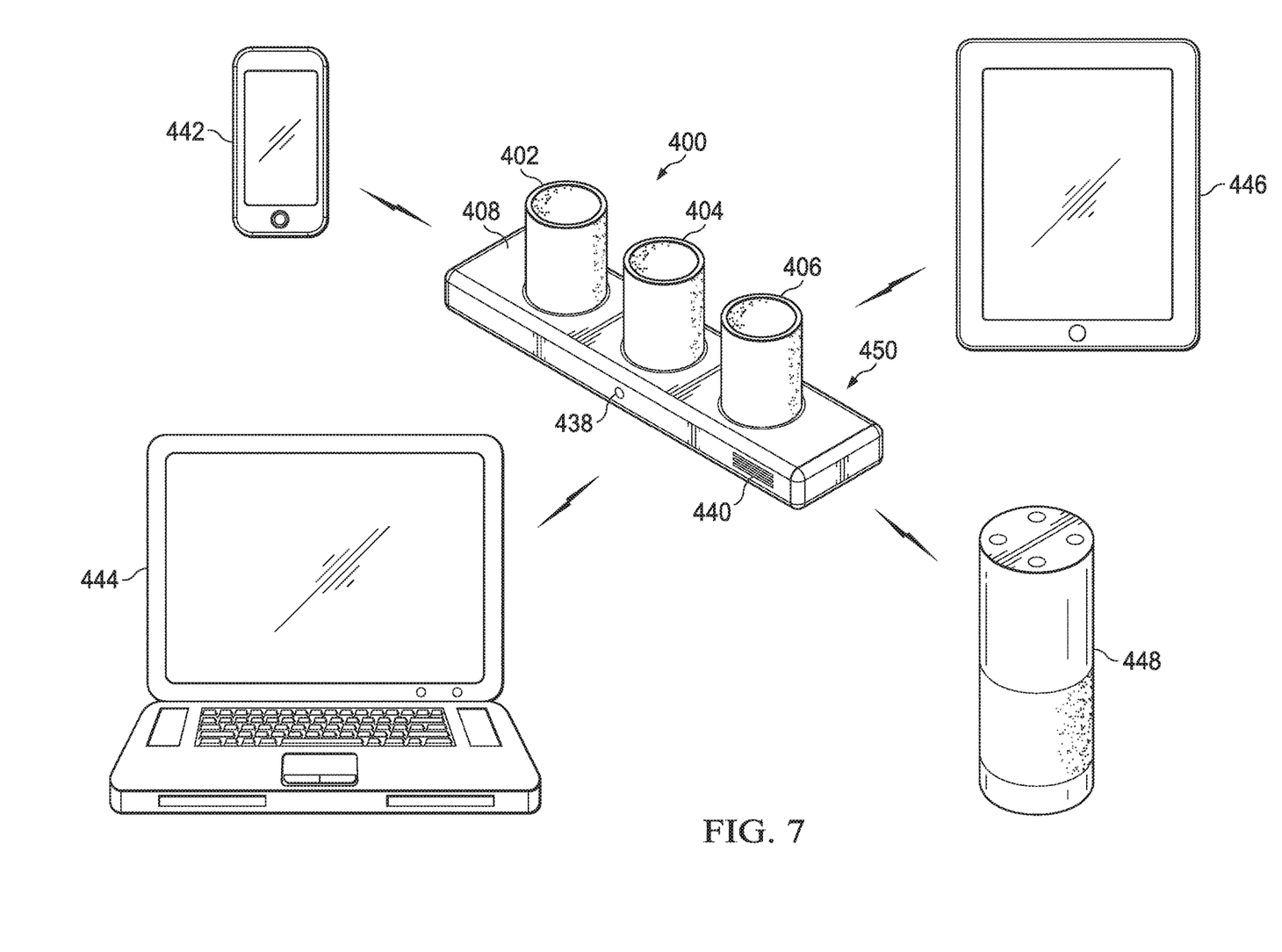
FIG. 7 shows another embodiment of a lighting device assembly interfacing with a plurality of external communication devices.

FIG. 7 depicts another system having a lighting device assembly 400 and external communication devices that are communicatively coupled to a network. In some embodiments, lighting device assembly 400 may communicatively couple to an external communication device having a user interface, such as a computer 444, a tablet 446, a phone 442, or voice-controlled device 448, by a cable, such as USB, USB-C, mini-USB, micro-USB, and the like. In other embodiments, lighting device assembly 400 may communicatively couple to an external communication device by a wireless network. The wireless network may be cellular (e.g., 2G, 3G, 4G, 5G, long-term evolution, etc.), Bluetooth®, ZigBee®, Wi-Fi, and other networks. One skilled in the art will recognize that any means of connecting and coupling components to allow communication signals to be transmitted and received may be implemented and that the external communication devices are depicted to illustrate the variation of devices that may be used in implementing the system.

Lighting device assembly 400 also includes an optical sensor 438 and a control module. In some embodiments, lighting device assembly 400 includes power management features to minimize power consumption while efficiently illuminating lighting device 400. The optical sensor 438 may facilitate power management features by allowing the control module to limit operation of lighting device assembly 400 based on the presence of a user.

During operation, optical sensor 438 determines whether a person is within a given distance. For example, the optical sensor 438 may use a light output and a light sensor to determine a range to the nearest object in the directed line or lines of sight. If the range is above a threshold distance based on the expected distance to a user, the control module may determine that a person is not present and terminate one or more features (e.g., heat sources 132 and 232, light sources 124 and 224, indicator 118, etc.) to limit power consumption while the user is not present.

The optical sensor 438 may continuously detect the relevant distance to the nearest object, and the control module may resume the operation of the features associated with the user's prior setting selection when the range detected by the optical sensor 438 indicates a person is present again. Alternatively, the optical sensor 438 may detect the relevant distance to the nearest object during a series of intervals to limit power consumption. One skilled in the art will recognize that other presence detectors (e.g., motion sensors, etc.) may be used with or instead of the optical sensor 438 to facilitate power management based on the presence of a user and that optical sensor 438 and the control module may be included in base 450 and lighting devices 402, 404 and 406.

In some embodiments, the optical sensor 438 is communicatively coupled to the control module by a wire. In other embodiments, the optical sensor 438 is communicatively coupled to the control module by a wireless network.

FIG. 7 also illustrates another method for dissipating excess heat emitted by lighting device assembly 400. Here, vents 440 are shown on a front part of top section 408 of base 450. Alternatively, vents 440 may be placed near the top edges of a bottom section of base 450. In some embodiments, vents 440 may allow excess heat emitted from components in base 450 (such as a circuit board, a heat source, etc.) to dissipate from base 450. In other embodiments, vents 440 may improve the dissipation of scented material 114 (shown in FIGS. 1 and 2) and increase the airflow from base 350.

In other embodiments, a user may insert scented material 114 (shown in FIGS. 1 and 2) into base 450 through an opening, such as vents 440. The opening may be a single opening or a plurality of openings and may vary in width and length depending on the desired appearance of base 450 and the size of scented material 114. The opening may be placed on a back part, side part or top part of top section 408 or bottom section of base 450.

The invention being thus described and further described in the claims, it will be obvious that the same may be varied in many ways. Such variations are not to be regarded as a departure from the spirit and scope of the invention, and all such modifications as would be obvious to one skilled in the art are intended to be included within the scope of the apparatuses and methods described herein.

The invention claimed is:

1. A system for a lighting device comprising:
a lighting device assembly comprising:
the lighting device having a retainer and a light source, wherein the retainer comprises a plurality of vertically spaced apart concentric rings, and wherein the plurality of vertically spaced apart concentric rings further comprise a plurality of indentions,
a base operably connected to the lighting device,
a heat source in the base, wherein the heat source is configured to heat a scented material in a vessel,
a control module and a network module; and
an external communication device having a user interface, wherein the lighting device and the external communication device are communicatively coupled to a wireless network and exchange data over the wireless network.

2. The system for the lighting device of claim 1, wherein the light source is a light emitting diode.

3. The system for the lighting device of claim 1, wherein the base comprises one of a touch button and an indicator.

4. The system for the lighting device of claim 1, wherein the lighting device further comprises one of a tilt sensor, a detachment sensor, a motion sensor, an accelerometer, a temperature sensor, a power sensor, a level sensor and an optical sensor.

5. The system for the lighting device of claim 1, wherein a temperature sensor is operably connected to the control module, and wherein the temperature sensor is configured to sense temperature of the heat source and the control module modifies an operation of the lighting device assembly based on a determination of whether the temperature meets a specified range.

6. The system for the lighting device of claim 4, wherein the control module turns the lighting device assembly off when the determination indicates that the temperature exceeds the specified range.

7. A lighting device assembly comprising:
a lighting device having a retainer and a light source;
a base operably connected to the lighting device, wherein the base comprises a top section, a bottom section and a sliding member;
a heat source in the base, wherein the heat source is configured to heat a scented material in a vessel;
a control module; and
a power source that is operably connected to the control module,
wherein the lighting device is removable from the base during operation of the lighting device and the base.

8. The lighting device assembly of claim 7, wherein the retainer comprises a plurality of concentric rings, and wherein the plurality of concentric rings further comprise a plurality of indentions.

9. The lighting device assembly of claim 7, wherein the light source is a light emitting diode.

10. The lighting device assembly of claim 7, wherein the power source is an external power source and the lighting device further comprises an internal power source, and wherein the internal power source charges when the lighting device is on the base.

11. The lighting device assembly of claim 7, wherein the lighting device further comprises one of a tilt sensor, a detachment sensor, a motion sensor, an accelerometer, a temperature sensor, a power sensor, a level sensor and an optical sensor.

12. The lighting device assembly of claim 11, wherein the power sensor is operably connected to the control module, and wherein the power sensor is configured to sense power consumption of the power source, and the control module modifies an operation of the lighting device assembly based on a determination of whether available power decreases below a threshold amount.

13. The lighting device assembly of claim 12, wherein the control module turns the lighting device assembly off when the determination indicates that the available power decreases below the threshold amount.

14. The lighting device assembly of claim 11, wherein the optical sensor is configured to sense distance to an object, and the control module modifies an operation of the lighting device based on a determination of whether the distance to the object indicates that a user is present.

15. The lighting device assembly of claim 14, wherein the control module turns the lighting device off when the determination indicates that the user is not present and turns the lighting device on when the determination indicates that the user is present.

16. A lighting device that comprises a translucent material, further comprising:
a retainer comprising a plurality of concentric rings, wherein the concentric rings comprise a plurality of indentions, wherein the translucent material of the lighting device adheres to the plurality of concentric rings around the plurality of indentions;
a light source mounted to the retainer, wherein the light source and the retainer are embedded within the lighting device;
a control module and a network module that are communicatively coupled to a wireless network; and
a power source operably connected to the network module.

17. The lighting device of claim 16, wherein the lighting device further comprises one of a tilt sensor, a detachment sensor, a motion sensor, an accelerometer, a temperature sensor, a power sensor, a level sensor and an optical sensor.

18. The lighting device of claim 16, wherein the power source is one of an internal power source and an external power source.

19. The lighting device of claim 16, wherein a user transmits an input to an external communication device, which exchanges data with the network module, and the control module modifies an operation of the lighting device based on the input.

\* \* \* \* \*